United States Patent [19]

Muhler et al.

[11] 4,418,053
[45] Nov. 29, 1983

[54] DENTAL PROPHYLAXIS COMPOSITIONS AND THEIR USE

[75] Inventors: Joseph C. Muhler, Howe; Mark S. Putt, Fort Wayne, both of Ind.

[73] Assignee: Indiana University Foundation, Bloomington, Ind.

[21] Appl. No.: 345,780

[22] Filed: Feb. 4, 1982

Related U.S. Application Data

[63] Continuation-in-part of Ser. No. 131,266, Mar. 17, 1980, abandoned.

[51] Int. Cl.³ .......................... A61K 7/16; A61K 7/18
[52] U.S. Cl. ........................................ 424/52; 424/49
[58] Field of Search ................................. 424/49–58, 424/52

[56] References Cited

U.S. PATENT DOCUMENTS

| | | | |
|---|---|---|---|
| 1,943,856 | 1/1934 | Cross | 167/93 |
| 2,059,396 | 11/1936 | Ripert | 167/93 |
| 2,216,821 | 10/1940 | Long | 167/93 |
| 2,384,563 | 9/1945 | Roseman et al. | 23/110 |
| 3,105,013 | 9/1963 | Saul et al. | 167/93 |
| 3,257,282 | 6/1966 | Muhler | 167/93 |
| 3,330,732 | 7/1967 | Muhler | 167/93 |
| 3,378,445 | 4/1968 | Muhler | 167/93 |
| 3,450,813 | 6/1969 | Muhler | 424/52 |
| 3,670,076 | 6/1972 | Muhler | 424/157 |
| 3,855,147 | 12/1974 | Granquist | 252/317 |
| 3,892,843 | 7/1975 | Muhler et al. | 424/52 |
| 4,064,231 | 12/1977 | Asakawa et al. | 424/52 |
| 4,108,979 | 8/1978 | Muhler et al. | 424/49 |
| 4,108,981 | 8/1978 | Muhler et al. | 424/55 |
| 4,122,163 | 10/1978 | Muhler et al. | 424/52 |

*Primary Examiner*—Shep K. Rose
*Attorney, Agent, or Firm*—Kirkland & Ellis

[57] ABSTRACT

The application discloses new dental prophylactic cleaning and polishing agents predominantly comprising magnesium metasilicate particles obtained by thermally treating selected minerals.

8 Claims, No Drawings

DENTAL PROPHYLAXIS COMPOSITIONS AND THEIR USE

CROSS REFERENCE

This application is a continuation in part of applicants' copending application, Ser. No. 131,266, filed Mar. 17, 1980, abandoned.

BACKGROUND OF INVENTION

1. Field of the Invention

The present invention relates to the field of dental prophylaxis and more specifically to new prophylactic cleaning and polishing agents and to the formation and utilization of prophylactic preparations incorporating such cleaning and polishing agents. In particular, the invention relates to prophylaxis paste cleaning and polishing compositions comprising selected mineral particles which are thermally processed.

These dental prophylaxis paste compositions have the ability to impart a smooth, highly polished surface to tooth enamel and to effectively remove all types of exogenous stains and accumulations from the teeth without resulting in undue abrasion of the enamel, dentin, or cementum. These compositions serve to clean and polish dental hard tissue in a novel manner such that reaccumulations of dental plaque and pellicle and occurrence and reformation of dental calculus on oral hard tissue are markedly reduced, thereby, significantly reducing the incidence of gingivitis and periodontal disease. Additionally, as a means of contributing to the partial control of dental caries, effective fluoride anticariogenic adjuvants, such as sodium fluoride, stannous fluoride, sodium monofluorophosphate, or acidulated phosphate fluoride, may be incorporated in such compositions. Other anticariogenic agents, such as aluminum carboxylates (U.S. Pat. Nos. 4,042,680 and 4,108,981), may also be advantageously employed in such compositions.

2. Description of the Prior Art

Dental research has developed substantial evidence that beyond the age of thirty years the loss of teeth is predominantly the result of periodontal involvement rather than dental caries. However, evidence in the dental literature indicates that gingivitis may be present in a large portion of the population as early as six to eight years of age. In this form, the disease is reversible. A major factor contributing to periodontal disease is the accumulation of certain forms of dental plaque and calculus on the teeth. These accumulations result in tissue inflammation of the surrounding gingiva, and, as the condition increases in severity, the periodontal fibers and supporting bone subsequently become affected. These reactions lead to the destruction of the supporting structures and the subsequent mass loss, in most instances, of sound teeth.

In the past, prophylaxis pastes have been used for the removal of exogenous stains that could not be removed by the routine use of a dentifrice and toothbrush, and other considerations, such as polishing ability, abrasiveness, and fluoride therapy, were regarded as secondary. Even at the present, many widely used dental prophylaxis products contain pumice, silica, or other hard materials of a relatively large particle size in order to achieve fast and thorough cleaning. It is apparent that excessive abrasion and scratching of the enamel increase the rate of reformation of exogenous stains and produce a low degree of enamel polish. It has been shown in several studies that a smooth, highly polished tooth surface is less receptive to reformation and retention of plaque, exogenous debris, pellicle, stains, and dental calculus.

Various abrasives have been employed for dental prophylactic treatment, but most appear to have significant disadvantages, both for the patient and the dentist or dental hygienist. For example, many are quite abrasive, some do not clean satisfactorily; the majority are inadequate polishing agents; and most, from a therapeutic viewpoint, have little, if any, supporting laboratory and clinical data demonstrating their effectiveness. Moreover, some products contain abrasives of high physical hardness and very low particle size that accelerate the normal attrition of the dental handpiece.

There are two essential characteristics that an improved abrasive system for use in a dental prophylaxis paste must possess in order to attain the desired properties. The first characteristic is the physical nature of the compound and how it relates to the physical functions of polishing, cleaning, abrasion, and scratching of the oral hard tissue. The relationship between cleaning, polishing, abrasion, and scratching induced by an abrasive agent is complex, and is dependent on a variety of properties of the abrasive: for example, chemical composition, crystal structure, cleavage, friability, hardness, particle shape, particle surface features, and particle size distribution. Obviously, high cleaning ability and low abrasion ae diametric opposites, as are high cleaning and high polishing. Thus, it is inevitable that some concessions must be made to achieve a suitable compromise, a fact that accounts for the large differences in cleaning, polishing, and abrasion of the various abrasives used in commercial prophylaxis pastes. The second characteristic is the chemical reactivity of the abrasive compound with fluoride adjuvants. Preferably, the abrasive should be chemically inert to fluoride (and stannous ion) in that the stability and therapeutic efficacy of different fluoride compounds are very dependent on the abrasive since it is the major component of any prophylaxis paste formulation. Fluoride is quite reactive and, depending on the particular abrasive compound, can react not only directly, as in addition and substitution reactions, but can be readily adsorbed onto the surface of the abrasive particles by electrostatic forces or can be associated with the surface in the form of a complex with a metal atom in the crystal lattice of the abrasive.

Although significant improvements in the polishing efficacy of prophylaxis compositions have been achieved in recent years through the use of zirconium silicate (U.S. Pat. Nos. 3,330,732 and 3,378,445), alumina (U.S. Pat. No. 3,670,076), and feldspar (U.S. Pat. No. 3,892,843), these agents still fall short of imparting maximum levels of polish during a typical, short prophylaxis treatment. Additionally, in order to achieve good cleaning properties with these materials, large particles are necessary; however, such particle sizes cause undesirably high abrasiveness an do not polish well. To obtain polishing, especially with alumina or zirconium silicate, it is necessary to include small-sized particles, which have little cleaning effect.

The beneficial effects, in terms of a reduction in the incidence of dental caries, resulting from the incorporation of water-soluble fluoride salts, such as sodium fluoride, stannous fluoride, sodium monofluorophosphate, or acidulated phosphate fluoride, are well known. However, efforts to utilize such salts in prophylaxis paste compositions have been handicapped by the tendency of fluoride and/or tin(II) ions to be inactivated and rendered unavailable by other ingredients, particularly the abrasive component of such compositions. In general, while prophylactic abrasives in therapeutic products used today are to varying degrees compatible with fluoride agents, there is a wide variation in compatibility. Abrasives containing polyvalent cations such as calcium and iron, either in their crystal structure or as impurities, are usually not particularly compatible.

Thus, prior art materials intended for use as cleaning and polishing constituents of prophylactic compositions have been unsatisfactory in one or more of the following respects, namely poor cleaning and polishing performances (especially with respect to inhibition of reaccumulation of dental calculus, pellicle, plaque, and exogenous stains), incompatibility with fluoride-containing anticariogenic agents, and adverse scratching and abrasion.

SUMMARY OF INVENTION

In accordance with the present invention, it has been found that new and more effective dental prophylactic preparations may be obtained by incorporating therein, as cleaning and polishing constituents, particles of selected minerals calcined at a temperature in the range of about 800° to 1200° C. to produce particles predominantly of the magnesium metasilicate form. In particular, the agents of this invention are obtained by calcining minerals selected from the smectite, sepiolite and chlorite groups characterized by superimposed layers of two-dimensional silica tetrahedra and two-dimensional octahedra, with the particles retaining a lamellar lattice structure after calcination.

Substantially none of the calcined particles is retained on an 80 mesh screen (177 microns) and essentially all pass through a 100 mesh screen (149 microns). Desirably, all of the particles are less than about 150 microns in diameter, and advantageously the median particle size lies in the range of 10–40 microns.

It has been discovered that selected mineral particles, when calcined at the desired temperature ranges and when prepared in the desired particle size ranges, can be used as a combined cleaning and polishing agent, overcoming the aforementioned problems of the prior art. Tests show that excellent cleaning and polishing results are obtained from a range of particle sizes within given limits, so that all particles participate in both functions, regardless of size. Cleaning and polishing are achieved with less scratching of the enamel surface than with prior materials. Also, it has been found that larger particles of the calcined minerals of this invention, in contrast to other dental prophylactic abrasives, are less abrasive than smaller particles of other materials, which accentuates the advantage.

It has further been found that the novel cleaning and polishing agents of the present invention may be used with nontoxic amounts of water-soluble anticariogenic adjuvants, such as sodium fluoride, stannous fluoride, sodium monofluorophosphate, or acidulated phosphate fluoride. In addition, with calcined mineral particles of this invention, the amount of anticariogenic agent added can be substantially reduced and yet superior reduction of enamel solubility is obtained. Such property has, among others, the advantage that taste problems are minimized or avoided.

It has likewise been discovered that application of prophylactic preparations of the present invention to the teeth provides a novel method for cleaning and polishing teeth and for reducing the incidence of gingivitis.

Through the use of the cleaning and polishing agents of the present invention, the difficulties experienced with prior art dental prophylaxis cleaning and polishing agents may be overcome, and compositions of the present invention may therefore be used to formulate prophylaxis pastes with superior cleaning and polishing capabilities and with enhanced anticariogenic ion compatibilities.

Accordingly, it is a primary object of the present invention to provide a new dental prophylactic cleaning and polishing agent capable of effectively removing pellicle and dental enamel exogenous stains and pigmentations and of polishing teeth to a heretofore unattainable level of luster in a minimum amount of time with minimal enamel scratching or abrasion.

Another object of the present invention is to provide a cleaning and polishing agent which is capable of reducing the reformation of dental plaque and calculus and the incidence of gingivitis and yet which is suitable for incorporation in a prophylaxis paste preparation.

Another object is to provide a dental prophylaxis paste that is suitable for cleaning and polishing both childrens' and adults' teeth.

A further object of the invention is to provide a dental prophylaxis paste adapted for use with a prophylactic cup which does not produce objectionable dental handpiece wear.

A still further object is to provide a prophylaxis paste preparation incorporating at least one fluoride-containing anticariogenic adjuvant in combination with a dental calculus-inhibiting cleaning and polishing agent of the character described which further serves to enhance the effectiveness of the anti-cariogenic adjuvant. It is yet another object to provide a dental prophylaxis paste including a fluoride-containing anti-cariogenic agent in which the quantity of fluoride can be substantially reduced, and yet which can produce better enamel solubility reduction, which unexpectedly is possible with certain calcined minerals as the cleaning and polishing agent.

It is a further object of the invention to provide a method for the effective cleaning and polishing of teeth with simultaneous anticariogenic fluoride treatment, which treatment does not cause gagging or emesis in patients.

These and other objects, advantages, and features of the present invention will hereinafter appear, and, for purposes of illustration, but not of limitation, exemplary embodiments of the subject invention are hereinafter described in detail.

DESCRIPTION OF PREFERRED EMBODIMENTS

In accordance with the subject invention, it has been found that optimal cleaning and polishing characteristics for a prophylaxis paste cleaning and polishing agent are exhibited by calcined particles of selected minerals. The mineral particles are ordinarily hydrated prior to calcining and after calcining are predominantly of the magnesium metasilicate form. (The term "magnesium metasilicate" is used interchangeably herein with the equivalent term "enstatite".)

In addition, it has been found that the cleaning and polishing compositions of the present invention may be advantageously used with water-soluble fluoride ion-containing anticariogenic adjuvants, such as sodium fluoride, stannous fluoride, sodium monofluorophosphate, or acidulated phosphate fluoride.

As a result of the foregoing, the calcined mineral particles of the character described find utility in therapeutic dental prophylaxis compositions (i.e. compositions containing at least one anticariogenic ionic adjuvant in combination with a compatible cleaning and polishing agent and designed to reduce the incidence and severity of dental caries) or in dental prophylaxis compositions which, although not containing fluorides or other anticariogenic agents, nonetheless have therapeutic utility in reducing gingival disease.

The particular minerals useful as prophylaxis paste cleaning and polishing agents in accordance with this invention are unique in three important ways. (1) Although the individual particles are too small and too soft for prophylaxis in their natural state, they unexpectedly form suitably large particles when calcined to specific temperatures far below their vitrification temperature. (2) The composition and structure of only a very few minerals of the myriad occurring in nature undergo the thermal transformation to the unique magnesium metasilicate end product, which has unequaled properties as a dental cleaning and polishing agent. (3) After calcination the mineral particles are unexpectedly compatible with fluoride adjuvants, a finding that is very surprising since magnesium compounds, including the uncalcined minerals of this invention, are, in general, incompatible with fluoride.

Composition and Structure of Uncalcined Species

The operative minerals of this invention are characterized by superimposed layers of two-dimensional silica tetrahedra of composition $Si_4O_6(OH)_4$ and two-dimensional octahedra consisting of two sheets of closely packed oxygens or hydroxyls in which aluminum, iron, or magnesium atoms are embedded in octahedral coordination. In the tetrahedral sheet aluminum may partly replace silicon (e.g., as in chlorite and saponite). Aluminum, in the octahedral sheet (known as the gibbsite structure when chemically balanced), may be replaced by magnesium (to form the brucite structure) or by other atoms such as iron, chromium, zinc, etc. These substitutions cause a negative charge imbalance which is compensated by adsorption of exchangeable cations (primarily $Ca^{++}$, $Na^+$ and $K^+$) on the layer surfaces since the cations are too large to be accommodated in the lattice interior.

The minerals of this invention are characterized by random magnesium substitutions in their lattices wherein the majority of the aluminum is replaced and there is minimal substitution of aluminum for silicon in the tetrahedral sheet. The magnesium-rich members of three mineral groups and their synthetic counterparts fulfill these criteria:

(1) the smectite group, comprising hectorite, $(Mg_{3-x}Li_x)Si_4O_{10}(OH)_2$, montmorillonite or bentonite, $(Al_{2-x}Mg_x)Si_4O_{10}(OH)_2$, the magnesium end member of which is stevensite, and saponite, $(Mg_{3-x}Al_x)(Si_{4-y}Al_y)O_{10}(OH)_2$;

(2) the sepiolite group, comprising sepiolite or meerschaum, $Mg_4Si_6O_{15}(OH)_2 \cdot 6H_2O$ and attapulgite, $Mg_5Si_8O_{20}(OH)_2 \cdot 8H_2O$; and (3) the chlorite group, comprising chlorite, $(Mg,Al,Fe)_6(Si,Al)_4O_{10}(OH)_8$.

Also included within the scope of this invention are synthetic equivalents of the foregoing naturally occurring minerals such as colloidal magnesium silicates, synthetic smectites similar in composition to saponite and hectorite, magnesium trisilicate $(Mg_2Si_3O_8)$, and amorphous hydrous magnesium silicate $(Mg_2Si_5O_{12})$. Accordingly, the terms "smectite," "sepiolite," and "chlorite" as used herein encompass their synthetic equivalents as well as the naturally occurring minerals falling within these groups.

In the smectite group, which has a layered mineral structure, each unit is composed of two silica tetrahedral sheets with a central octahedral sheet. The tetrahedral and octahedral sheets are combined so that the tips of the silica tetrahedrons and the hydroxy groups of the octahedral sheet form a common layer. These "sandwich" units when stacked are held together by very weak bonds and are easily cleaved. The outstanding feature of the smectites is that water and other polar molecules can penetrate between unit layers, causing the lattice to expand. In the absence of any charge imbalance on the lattice (as in the case of talc and pyrophyllite), there is no intercrystalline swelling. The theoretical formula of smectite without considering lattice substitutions is $Al_4Si_8O_{20})(OH)_4 \cdot nH_2O$, but smectite always differs from theoretical because of aluminum substitution for silicon in tetrahedral coordination and/or magnesium, iron, zinc, nickel, lithium, etc. for aluminum in the octahedral sheet. In the tetrahedral sheet aluminum substitution for silicon is normally less than 15%. In the theoretical formula only two-thirds of the possible positions in the octahedral sheet can be filled by aluminum; smectites of this type are called dioctahedral. The replacement of $2Al^{+3}$ by $3Mg^{+2}$ in the octahedral sheet yields the mineral saponite. Any aluminum in saponite replaces silicon in the tetrahedral sheet. Layer minerals of this type in which all the possible octahedral positions are filled are called trioctahedral and are the preferred smectite species of this invention. However, a substantially pure trioctahedral hydrous magnesium silicate named stevensite is known to exist. Hectorite, which contains no aluminum, has some lithium substitution for magnesium. Electron micrographs of montmorillonites reveal a variability in the shape of the particles. Some are broad, undulating mosaic sheets which break easily into irregular masses of extremely small particles while others are irregular flake-shaped aggregates which sometimes have curled edges. Some of the magnesium-rich members of the smectite groups, such as saponite, are composed of equidimensional flake-shaped particles. Hectorite, on the other hand, is found in thin laths which tend to lose their identity in aggregates.

The sepiolite group is characterized by a ribbon structural array. The units are composed of double chains of silica tetrahedra linked together through oxygens at their longitudinal edges so that the apexes of the tetrahedrons in successive chains point in opposite directions. The linked chains, therefore, form a kind of double-ribbed sheet with two rows of tetrahedral apexes at alternate intervals in the top and bottom of the sheets. The ribbed sheets are arranged so that the apexes of successive sheets point together, and the sheets are held together by aluminum and/or magnesium in octahedral coordination between the apex oxygens of successive sheets. The octahedral layer is similar to that in the layered minerals, but is continuous in only one direction. Cleavage occurs through the common oxygens of the silica chains in the ribbed layer. Chains of water molecules fill the interstices between the chains. The major structural difference between attapulgite and sepiolite is that in the sepiolite structure there is an extra silica tetrahedron added at regular intervals to the chains on each side of the unit. Unlike the smectites, neutrality is maintained in the structure by the presence of sufficient additional protons and/or exchange ions to balance any residual charge deficiency. Some substitution of aluminum for both silicon and magnesium occurs in attapulgite. Sepiolite does not have appreciable aluminum substitution and for this reason, coupled with the fact that low-iron deposits are commercially available, is the preferred species of this invention. Electron micrograph of these minerals show elongate lath-shaped particles and bundles of laths, where those of sepiolite are thicker and shorter than those of attapulgite. At high magnification the exterior of the laths exhibits a gutter-and-channel appearance. Tangling of individual laths produces an interwoven aggregate mass that is sometimes manifested in paper-like flakes.

The chlorites are defined as mixed layer clay minerals. All true chlorites have the same general structural framework consisting of alternate talc-like and brucite-like layers between which exists basal cleavage. The talc-like layers are trioctahedral and may be unbalanced by substitution of aluminum for silicon. This deficiency of charge is balanced by an excess charge in the brucite sheet due to substitution of aluminum and iron for magnesium. Various members of the chlorite group differ from each other in the kind and amount of substitutions within the brucite layer and the tetrahedral and octahedral positions of the talc layer. They also differ in the detailed orientation of successive tetrahedral and octahedral layers, in the relation of the talc to brucite layers, and in the stacking of successive chlorite units. The chlorite particles exist as small, poorly defind flakes commonly grouped together in irregular aggregates. In general, the electron micrographs resemble those of montmorillonite, but the particles are larger and thicker with better-defined edges.

Dehydration and Changes Resulting from Heating

Because of their slightly different crystal structures and their variability in composition due to lattice substitutions and impurities, the mineral groups of this invention differ somewhat in the way they dehydrate and the temperatures of phase change. Dehydration and phase changes are determined by weight loss, differential thermal analysis, and x-ray diffraction. A brief summary of the properties of each group is provided below.

The smectites lose considerable water at low temperatures (100°-200° C.). The amount, which occurs mostly as interlayer water between silicate sheets, is contingent upon the nature of adsorbed ions. Magnesium montmorillonites pass through stable hydrates as the temperature is increased. The dehydration curves usually show no distinct break between the loss of the last interlayer water and the beginning of loss of lattice (i.e. hydroxyl) water. The temperature of loss of hydroxyl water varies widely among smectites, beginning as low as 400° C. for iron montmorillonites to as high as 700° C. for hectorite. Dehydroxylation and the accompanying endothermic reaction vary substantially depending on the exchangeable cations. X-ray diffraction data show little change curing dehydration, indicating that the silicate structure is unchanged. In fact, the structure of dioctahedral smectites persists to 800°-900° C. where lattice destruction correlates with the endothermic reaction observed in this temperature range. The variation in crystalline phases that develop at high temperatures is due primarily to composition differences as well as exchangeable ion composition. Following the loss of hydroxyl water during the calcination process, the first high-temperature phase changes are largely determined by the structural attributes of the mineral itself and are not necessarily the results expected from phase-diagram considerations and bulk chemical composition, but are due primarily to "inheritance" from the original mineral structure. In other words, rather than complete phase conversion to enstatite and other possible end products, depending on composition, the mineral maintains a lamellar structure which undergoes gradual destruction as nucleation of the end product commences when the temperature is increased. Thus, a unique structure can result at specific temperatures for each precursor due to incomplete phase changes, wherein the bulk of the particle retains its dehydrated mineral-lameller structure and its periphery transforms into micro-crystallates of the high-temperature phase, i.e., enstatite. When analyzed by x-ray diffraction, the smectite samples of this invention generally showed the formation of enstatite at 1000° C., which coincided with improved enamel polishing properties and better fluoride compatibility.

Members of the sepiolite group have large water loss below 100° C. and gradual continuous loss up to about 800° C. Differential thermal analysis indicates that adsorbed water in the channels is lost at 275°-375° C., and hydroxyl water is lost from 550° to 800° C., resulting in lattice contraction in both directions. X-ray diffraction analysis reveals no change in structure until 350° C. where a modified form persists until approximately 700° C., when it passes into a transient amorphous phase. The sepiolite structure is lost at about 800° C. when an exothermic reaction indicates the nucleation of enstatite which develops slowly as the temperature is increased. Cristobalite, although reported to form in some samples as low as 1075° C., was not detected in the samples of this invention.

The chlorite minerals have little water loss until approximately 500° C. when considerable loss occurs. Water loss is variable above 600° C. and dehydration is complete at 850°-900° C. Differential thermal analyses demonstrate little or no low-temperature endothermic reactions, indicating an absence of interlayer or adsorbed water. However, endothermic peaks at 500°-700° C. and at approximately 800° C. indicate that hydroxyl water is driven off in two stages, first from the brucite layer and second from the talc layer. The dehydration temperature varies depending on the cation in the octahedral layers of both the brucite and talc part of the structure. Magnesium-rich chlorites cause higher temperatures of dehydration. During dehydration up to 700° C., x-ray diffraction data indicate a gradual breakdown of the brucite layer while the talc layer remains unchanged. Above 700° C. the magnesium atoms migrate to positions adjacent to the talc-unit surface and as the temperature increases, the talc layer dehydrates causing total destruction of the chlorite structure followed by olivine crystallization which correlates with an exothermic reaction at 800°-900° C. Other phases, such as enstatite and spinel form at temperatures above 900° C., depending on composition.

Theoretical Explanation of Unique Dental Properties

The uniqueness of the calcined mineral cleaning and polishing agents of this invention for use as dental prophylaxis abrasives is belived to be due to the retention by the magnesium-rich minerals of the smectite, sepiolite, and chlorite groups of their lamellar lattice structure after dehydration and dehydroxylation. This permits the formation of the preferred magnesium metasilicate (enstatite) phase in a layered structure where nucleation appears to begin on the periphery of the individual particles. Particles of this type behave differently than irregularly shaped, conventional particles, such as pumice, when physically applied to the teeth. That is, being of a lamellar platelet or lath-form the individual particles are more two-dimensional and tend to lie flat when physically applied to the tooth surface so that the enstatite micro-crystallates on the surface of the particle polish the tooth as they are moved across it. Conversely, conventional abrasives are more three-dimensional and have the tendency to tumble and gouge the tooth surface when physically applied, thus polishing less uniformly and causing greater abrasion of the enamel substrate. In addition, enstatite is only slightly harder than tooth enamel, thus permitting polishing activity with little substrate loss.

Improved cleaning properties are attributable to the fused aggregates that are formed by calcining. Individual mineral particles are very small (i.e. less than 2 microns) which makes them unsuitable as an abrasive agent for dental prophylaxis. However, the individual particles, which exist as stacked aggregates or interwoven mats before calcination, evidently undergo peripheral fusion to form suitably large particles when calcined at 900°-1200° C. This phenomenon is unique to the materials of this invention since other clay minerals (e.g. kaolinite) do not form fused aggregates until sintering begins at temperatures of greater than 1200° C. This phenomenon appears to be caused by the superimposed sandwich structure of the tetrahedral and octahedral layers and the high magnesium content, which together permit the ready formation of Mg-Si bonds due to the close proximity of the silica tetrahedra and brucite octahedra after dehydration. Moreover, the presence of exchangeable cations ($Li^+$, $Na^+$, $K^+$, etc.) adsorbed onto the layer surfaces may facilitate peripheral fusion by action as a flux. Additionally, the aggregate particles contribute to rapid polishing with low abrasion of tooth enamel as a result of their friability; that is, they readily break down into smaller units performing their initial cleaning and polishing function, after which polishing continues with very little wear to enamel.

The low reactivity with fluoride compounds of the calcined magnesium silicates of this invention is probably attributable to the strength of the magnesium-silicon bond in the lattice formed after dehydration. Magnesium ions, which readily react with fluoride in solution to form the very slightly soluble salt, $MgF_2$, are tenaciously bound in the silicate lattice and consequently are unavailable to react with fluoride.

In accordance with this invention the selected mineral particles are calcined at a temperature lying in the range of about 800° C. to 1200° C. Calcining may be achieved by heating in saggers in a furnace or by means of a rotary kiln wherein the degree of calcination may be controlled by altering the feed rate of material to the calciner, by varying the calcination residence time or the thickness of the material bed in the calciner, or by other methods known in the art. If the temperature does not reach 800°-900° C., the selected minerals do not undergo the phase conversion to the preferred metasilicate form and thus are insufficiently hard to clean and polish satisfactorily from a dental standpoint. Material which has been calcined in the range of 800° to 1000° C. is predominantly magnesium metasilicate in the form of enstatite-type crystals. However, if more highly calcined (i.e. is subjected to temperatures of up to about 1200° C.), materials such as cristobalite ($SiO_2$) are formed. The amount of cristobalite formed is dependent on the ratio of magnesium to silicon on the starting material. The higher the magnesium content, the more favored is the production of the preferred magnesium metasilicate form. Magnesium metasilicate (enstatite) is the preferred reaction product because of its lower hardness and unique lamellar crystal structure. Material containing large amounts of cristobalite is unsatisfactory from a dental standpoint because of its tendency to abrade the tooth enamel unless reduced in size by milling or grinding. As a consequence, the calcined minerals of this invention are predominantly of the magnesium metasilicate (enstatite) form.

After calcining, many of the materials agglomerate into large masses and grinding and/or milling are required to obtain a cleaning and polishing agent having a particle size distribution lying in the range found to be useful in dental prophylaxis compositions. Economical dry grinding processes such as conventional ball-milling may be employed, followed by screening through standard mesh sieves to separate incompletely degraded agglomerates. The preparation of suitably sized particles of the calcined minerals may also be accomplished by other conventional techniques well known in the art.

The calcined mineral particles of the present invention have a particle size range such that substantially none of the particles is retained on an 80 mesh screen (177 microns) and the size range is essentially less than 100 mesh (149 microns). Preferably, the particle size distribution falls into the ranges as shown in Table 1 which were determined by means of a Micromerograph.

TABLE 1

| Particle Size Distribution Range of Calcined Mineral Particles | |
| --- | --- |
| Particle Size | Weight (%) |
| >70 | 0-10 |
| >60; <70 | 0-10 |
| >50; <60 | 0-15 |
| >40; <50 | 2-20 |
| >30; <40 | 5-25 |
| >20; <30 | 5-25 |
| >10; <20 | 10-40 |
| >5; <10 | 5-30 |
| <5 | 0-20 |
| Median | x = 10-40 microns |

Cleaning and polishing without serious scratching are pronounced when the particle size range is such that a majority of the particles by weight pass through a 200 mesh screen. Within the indicated size range, the particles are effective for both cleaning and polishing. Hence, it is unnecessary to be meticulous in proportioning large and small particles so as to obtain a blend that can both clean and polish teeth. The value of this can be better understood by recognizing that for prophylactic cleaning and polishing of children's teeth, very little actual scouring is required, but polishing is important because immature teeth have a low luster. In contrast, whereas for adult's teeth, which are often stained by tobacco, coffee, tea, etc., substantial cleaning ability is required. With prior art cleaning and polishing agents, separate mixes of finer particle sizes are made to avoid excessive and unnecessary scratching and abrasion of the teeth, and other mixes of larger sized particles are made to perform the difficult cleaning adequately.

With the calcined mineral particles of the present invention, it is possible to use a single overall size range of particles for both children's and adult's teeth. Moreover, in both situations the degree of abrasivity or scratching to the oral hard tissues is less than with prior art materials. Thus, this product is considerably safer to use than prior art materials, because it cleans and polishes as well or better than prior art materials with less deleterious abrasion and scratching.

The cleaning and polishing agents of the present invention may be applied directly to the teeth as a powder in aqueous slurry form. However, it is preferred that the agent be applied in the form of a prophylaxis paste composition. The cleaning and polishing agent is provided in the paste composition within a range of about 30-95% by weight of the overall composition, depending upon the particular formulation desired, as is well known to one skilled in the art. Where desired, a portion of the calcined minerals of this invention or combinations thereof may be replaced by compatible fillers, extenders, or other abrasives such as uncalcined minerals, aluminum silicates, alumina, zirconium silicate, insoluble sodium metaphosphate, silicas, etc., and mixtures of these other agents as well as other dental abrasive materials. The prophylaxis paste may be prepared in a conventional manner and usually includes additional ingredients that render the overall composition commercially acceptable. For example, prophylaxis pastes typically contain conventional components such as water, binders, humectants, flavoring agents, sweeteners, detergents, and the like, in the range of up to approximately 50% by weight. Through the use of a prophylaxis paste of the character described, it is possible to obtain clean, yet highly polished, oral hard tissues during the infrequent (i.e., semi-annual) professional prophylaxis treatments performed by a dentist or dental hygienist.

Furthermore, it is preferred that anticariogenic agents be incorporated in such prophylaxis pastes so that the advantages of such agents may be obtained in addition to the cleaning and polishing advantages of the abrasive component. The anticariogenic agent may comprise one or more water-soluble fluoride salts, including NaF, $SnF_2$, $Na_2PO_3F$ as well as acidulated phosphate fluoride (APF) mixtures. Other suitable fluoride adjuvants include KF, LiF, $SnF_4$, $InF_3$, $PbF_2$, $FeF_2$, $TiF_4$, and $NH_4F$, as well as more complex water-soluble fluoride-containing adjuvants such as fluorosilicates, e.g. $Na_2SiF_6$; fluorozirconates, e.g. $CaZrF_6$, $Na_2ZrF_6$, $K_2ZrF_6$, $SnZrF_6$, $InZrF_7$; fluorostannites, e.g. $NaSnF_3$, $KSnF_3$, $NaSn_2F_5$; fluoroborates, e.g. $NaBF_4$; fluorotitanates, e.g. $NaTiF_5$; fluorogermanates, e.g. $K_2GeF_6$, $Zr(GeF_6)_2$, $ZrOGeF_6$, $In_2(GeF_6)_3$; and mixed halides, e.g. $SnClF$ and $Sn_2ClF_3$.

When used in combination with a fluoride-containing anticariogenic adjuvant in aqueous solution, the tendency of the calcined mineral particles of the present invention to react with or deactivate the fluoride adjuvant is substantially nil. Because of the compatibility of these cleaning and polishing agents with fluoride compounds throughout the biologically feasible pH range, the anticariogenic effect of the fluoride can be obtained using lower concentrations of the adjuvant than heretofore possible with prior art dental prophylactic abrasives. This eliminates or at least reduces bad flavor problems and the nauseating effects of conventional larger quantities of fluoride-containing adjuvants, especially stannous fluorides.

Fluoride-containing adjuvants are employed in pastes of the invention at a non-toxic concentration sufficient to significantly reduce the incidence of dental caries in patients. This concentration may range widely, and depends, at least in part, upon the nature of the chosen adjuvant. In general, satisfactory results may be obtained within the range of about 0.1 to 20% by weight of the paste composition (calculated as fluoride ion). When NaF, $Na_2PO_3F$, or HF are utilized, such compounds are preferably employed at levels of about 0.5 to 5% by weight of the paste. With $SnF_2$ a concentration range of approximately 1 to 10% is acceptable.

Advantageously, a source os stable phosphate (e.g. phosphoric acid or sodium orthorphosphates) may be used in conjunction with the fluoride agent in order to enhance its anticariogenic activity.

In addition, other suitable anticariogenic adjuvants, such as the aluminum carboxylate complexes described in U.S. Pat. Nos. 4,042,680 and 4,108,981 and other non-toxic water soluble sources of aluminum ions may also be employed to produce anticariogenic prophylaxis paste compositions in accordance with the subject invention.

Compositions of exemplary prophylaxis paste preparations employing the cleaning and polishing agents of the present invention are given in the following examples:

EXAMPLE 1

| Constituent | % by Weight |
| --- | --- |
| Sepiolite (calcined at 1100° C.) | 45.0 |
| Distilled Water | 20.9 |
| Glycerin | 15.0 |
| Sorbitol (70% aqueous solution) | 16.0 |
| Veegum (Magnesium aluminum silicate) | 0.5 |
| Sodium Carboxymethyl Cellulose | 1.0 |
| Sodium Saccharin | 0.5 |
| Flavor | 1.0 |
| Methyl p-hydroxybenzoate | 0.1 |
| | 100.0% |

EXAMPLE 2

| Constituent | % by Weight |
| --- | --- |
| Hectorite (calcined at 900° C.) | 52.1 |
| Distilled Water | 18.0 |
| Propylene Glycol | 20.0 |
| Hydroxyethyl Cellulose | 0.9 |
| Sodium Saccharin | 1.0 |
| Flavor | 2.0 |
| Trisodium Citrate | 1.0 |
| Stannous Fluoride, $SnF_2$ | 5.0 |
| | 100.0% |

EXAMPLE 3

| Constituent | % by Weight |
| --- | --- |
| Chlorite (calcined at 1200° C.) | 51.0 |
| Distilled Water | 19.5 |

-continued

| Constituent | % by Weight |
|---|---|
| Glycerin | 4.7 |
| Propylene Glycol | 12.5 |
| Sorbitol (70% aqueous solution) | 2.7 |
| Bentone (Organo-clay gellant) | 1.5 |
| Sodium Saccharin | 0.4 |
| Flavor | 0.6 |
| Sodium Fluoride, NaF | 4.0 |
| Sodium Dihydrogen Phosphate, $NaH_2PO_4$ | 2.3 |
| Miscellaneous | 0.8 |
| | 100.0% |

Experimental Evaluations

The superiority of the calcined mineral particles as prophylaxis cleaning and polishing agents as compared with other abrasives has been substituted by the following experimental evaluations.

Testing was performed with an instrument designed specifically for the purpose of evaluating prophylactic compositions. This device has an adjustable velocity motor-mandrel assembly to which the prophylactic cup is attached, the entirety of which can be automatically moved laterally back and forth by means of a flexible shaft-step motor arrangement. The extent of the lateral movement is precisely controlled by limit switches adjustable to 0.01 inch. The specimen is positioned in a round cup and is held in place by means of a permanent magnet. The specimen cup is revolved by means of a flexible shaft-variable speed motor assembly, and is positioned on the pan end of a triple-beam balance that enables the precise adjustment of pressure. The prophylactic cup motor assembly is lowered onto the specimen and the height of the specimen cup is adjusted by means of a screw until the force is sufficient to balance the weighted arm of the triple-beam balance. During treatment of prophylactic cup is automatically raised every ten seconds from the specimen surface to simulate slurry replenishment during prophylaxis. For the polishing and abrasion evaluations abrasive slurries were prepared by mixing two parts of a 1% sodium carboxymethyl cellulose solution with one part of abrasive by weight in order to prevent the abrasive from settling.

Polishing evaluations were made with bovine permanent incisors mounted in Wood's metal with the labial surface exposed. The labial surface was leveled by means of a mechanical surface grinder so as to provide a smooth, uniform area for testing that was not into the dentin and was parallel to the base. The teeth selected were of sufficient size to provide a leveled area approximately 1.0 cm in diameter. The mounted tooth specimens were dulled by immersion in 0.2 M HCl for thirty seconds, followed by thorough rinsing with distilled water. The specimens were mechanically treated by means of a simulated prophylaxis where the prophylactic cup was rotated under a load of 300 grams at 1000 rpm and oscillated ±0.14 inch from the zero position at a rate of five cycles per minute, and the specimen cup revolved at 30 rpm. This procedure produced a uniformly randomized treatment pattern that ensured reproducibility between replicates. Treatment times were varied from ten seconds to cumulative times of twelve minutes.

The reflectance of the polished tooth surface was determined by means of a reflectometer designed to detect changes in the degree of luster of the enamel surface. This instrument produces a beam of light which, when reflected from the leveled tooth surface, impinges on a photoelectric cell which in turn activates an X-Y recorder, producing a graphical print-out of the entire leveled tooth surface. The smoother and more highly polished the enamel surface, the smaller is the amount of diffused and absorbed light and, hence, the higher the reflectance reading. The reflectometer was calibrated so that 0 represented total darkness and 100 was set to white carrara glass standards, and the data for the abrasives tested hereinafter are reported on this scale.

The harmfulness of a prophylactic abrasive can be expressed in terms of dentin and enamel abrasion values. Dentin and enamel abrasion values for prophylaxis paste cleaning and polishing agents were determined using bovine teeth. Dentin specimens were prepared by sagittally sectioning bovine permanent incisors throught the pulp cavity, carefully trimming off the enamel around the perimeter, and mounting the anterior half in a block of self-curing acrylic with the exposed dentin facing upward. The dentin was ground flush with the acrylic surface using a model trimmer and a coarse wheel. The ground surface was then uniformly smoothed and leveled with a mechanical surface grinder. The dentin specimens were treated for a total of two minutes using the prophylaxis instrument as described previously for enamel polish. Enamel abrasion specimens were prepared by immersing trimmed bovine incisors in dental acrylic with the labial surface facing upward. The blocks were ground, using a model trimmer and coarse grinding wheel, until the enamel was leveled to an area approximately 9 mm in length and was flush with the acrylic. Further smoothing and flattening were accomplished with a mechanical surface grinder, then a very smooth, optically polished surface was produced using 0.3 micron alpha alumina on a horizontal polishing wheel with a silk cover. The enamel specimens were treated for a total of five minutes using the prophylaxis instrument to administer a reciprocating treatment wherein the specimen was not revolved but maintained stationary while the prophylactic cup made repeated passes over it. All other treatment conditions were the same as described previously.

The amount of dentin or enamel removed by each abrasive under identical treatment conditions was used as an indicator of abrasivity and was quantitatively measured by means of a proficorder, a surface profile measuring device. The proficorder has a diamond stylus which, when tracing the surface of a specimen, produces an electrical signal proportional to the irregularities on the traced surface. These signals are amplified and converted into a graphical form on a strip chart producing a very sensitive, accurate record of the surface microtopography. By superimposing before-and after-treatment traces, the cross-sectional area of abrasion was visualized and was measured by means of a planimeter. From this value the mean abraded depth of each specimen was calculated, and both the dentin and enamel abrasion data are hereinafter reported in this fashion.

The effectiveness of a dental abrasive as a compatible carrier vehicle for fluoride-containing adjuvants was determined by measuring the amounts of available fluoride and tin(II) ions in solution. Percentage availability refers to a comparison of an ionic concentration level with a reference solution of the adjuvant without the carrier vehicle. A percentage ratio of the ionic concentration level detected for each abrasive agent was determined by adding 8.00 grams of abrasive to a 20 ml aliquot of 1000 ppm fluoride solution, mechanically shaking for fifteen minutes, centrifuging until clear, and decanting. The supernatant was analyzed for fluoride with a fluoride electrode and for tin(II) by means of an iodimetric titration. Thus, for example, a combination solution of abrasive (carrier vehicle) and sodium fluoride which analyzed 900 ppm fluoride concentration compared to a reference solution of sodium fluoride at 1000 ppm fluoride exhibits at 90% availability.

Enamel polish data were obtained for a number of prophylaxis abrasives in accordance with this invention. For comparative purposes, data were also obtained for several conventional prophylaxis abrasives as well as a number of other materials not encompassed by this invention. These data, which are provided in Table 2, show the superior polishing characteristics of the calcined mineral particles of this invention.

Several of these polishing agents and a number of conventional prophylaxis abrasives were also examined for their rate of enamel polishing ability (i.e. polish versus treatment time). These data, which are reported in Table 3, demonstrate that the materials of this invention produce more rapid rates of polish and higher luster maximums than conventional abrasives used for dental prophylaxis.

TABLE 3
ENAMEL POLISH RATE OF CALCINED MINERALS AND OTHER ABRASIVES

| Polishing Agent | Calcining Temperature | Polish Score (vs. Treatment Time in Minutes) | | | | | | |
|---|---|---|---|---|---|---|---|---|
| | | 1/6 | ½ | 1 | 2 | 4 | 8 | 12 |
| Amorphous Hydrous Magnesium Silicate | 1000° C. | 52 | 98 | 106 | 109 | 112 | 112 | 114 |
| Hectorite | 900° C. | 81 | 100 | 107 | 113 | 114 | 119 | 120 |
| Magnesium Trisilicate | 900° C. | 51 | 90 | 100 | 106 | 111 | 113 | 115 |
| Sepiolite | 1000° C. | 80 | 103 | 112 | 116 | 116 | 119 | 118 |
| Cristobalite | — | 39 | 70 | 81 | 90 | 98 | 102 | 105 |
| Feldspar | — | 50 | 76 | 89 | 98 | 105 | 108 | 109 |
| Pumice, Coarse | — | 32 | 54 | 69 | 84 | 87 | 94 | 94 |
| Pumice, Fine | — | 46 | 64 | 79 | 89 | 96 | 97 | 100 |
| Pumice, Flour | — | 51 | 75 | 86 | 92 | 98 | 103 | 105 |
| Quartz | — | 45 | 71 | 90 | 102 | 106 | 107 | 111 |
| Zirconium Silicate | — | 64 | 85 | 98 | 106 | 111 | 113 | 115 |

TABLE 2
ENAMEL POLISH OF CALCINED MINERALS and OTHER ABRASIVES

| Polishing Agent | Calcining Temperature | Polish Score* (30-Second Treatment) |
|---|---|---|
| Amorphous Hydrous Magnesium Silicate | Uncalcined | 64 ± 2 |
| | 900° C. | 87 + 3 |
| Hectorite | 900° C. | 99 ± 3 |
| Magnesium Trisilicate | Uncalcined | 48 ± 6 |
| | 900° C. | 89 ± 5 |
| Sepiolite | Uncalcined | 35 ± 0 |
| | 1000° C. | 103 ± 3 |
| Chlorite | Uncalcined | 38 ± 2 |
| | 1200° C. | 91 ± 3 |
| Saponite | 900° C. | 94 ± 2 |
| Cristobalite, SiO2 | — | 62 ± 5 |
| Feldspar, (Na,K)AlSi3O8 | — | 76 ± 3 |
| Magnesium Carbonate, MgCO3 | — | 45 ± 3 |
| Magnesium Hydroxide, Mg(OH)2 | — | 40 ± 3 |
| Magnesium Oxide, MgO | — | 62 ± 2 |
| Magnesium Phosphate, Mg3(PO4)2 | — | 49 ± 1 |
| Pumice, Coarse | — | 53 ± 1 |
| Pumice, Fine | — | 67 ± 3 |
| Pumice, Flour | — | 72 ± 2 |
| Quartz, SiO2 | — | 65 ± 3 |
| Zirconium Silicate, ZrSiO4 | — | 74 ± 2 |

*Mean + Standard Error.

Enamel and dentin abrasion data were obtained for several calcined minerals and conventional prophylaxis abrasives and are reported in Table 4. The data in Table 4 show that the materials of this invention are of low abrasivity to both enamel and dentin.

TABLE 4
ENAMEL AND DENTIN ABRASION OF CALCINED MINERALS AND OTHER ABRASIVES

| Polishing Agent | Calcining Temperature | Enamel Abrasion* Score(micro-in.) | Dentin Abrasion* Score(micro-in.) |
|---|---|---|---|
| Amorphous Hydrous Magnesium Silicate | 1000° C. | 81 ± 16 | 2031 ± 283 |
| Sepiolite | 1000° C. | 38 ± 11 | 715 ± 81 |
| Feldspar | — | 90 ± 40 | 1832 ± 151 |
| Pumice, Coarse | — | 967 ± 114 | 3245 ± 205 |
| Pumice, Fine | — | 822 ± 67 | 3068 ± 478 |
| Pumice, Flour | — | 476 ± 161 | 2634 ± 327 |
| Zirconium Silicate | — | 269 ± 57 | 1861 ± 55 |

*Mean ± Standard Error.

Fluoride availability data were determined for a number of prophylaxis abrasives in accordance with this invention. For comparison, data were also obtained for conventional prophylaxis abrasives and several other materials not included in this invention. These data, which are provided in Table 5, demonstrate the high degree of compatibility of the calcined magnesium silicates with three different fluoride-containing adjuvants.

TABLE 5
FLUORIDE COMPATIBILITY OF CALCINED MINERALS AND OTHER ABRASIVES

| Polishing Agent | Calcining Temperature | Percent Availability | | | |
|---|---|---|---|---|---|
| | | $F^-$(as NaF) | $F^-$(as APF) | $F^-$(as $SnF_2$) | $Sn^{++}$(as $SnF_2$) |
| Amorphous Hydrous Magnesium Silicate | Uncalcined | 81.3 | 34.5 | 67.2 | 0.2 |
| | 1000° C. | 99.7 | 100.3 | 97.7 | 96.7 |

TABLE 5-continued
FLUORIDE COMPATIBILITY OF CALCINED MINERALS AND OTHER ABRASIVES

| Polishing Agent | Calcining Temperature | Percent Availability | | | |
|---|---|---|---|---|---|
| | | F⁻(as NaF) | F⁻(as APF) | F⁻(as SnF$_2$) | Sn⁺⁺(as SnF$_2$) |
| Hectorite | 1100° C. | 100.4 | 94.8 | 99.2 | 91.8 |
| Magnesium Trisilicate | Uncalcined | 25.1 | 5.8 | 12.4 | 0.2 |
| | 1100° C. | 99.3 | 99.6 | 98.7 | 83.8 |
| Sepiolite | Uncalcined | 43.8 | 31.3 | 31.6 | 0.2 |
| | 1100° C. | 99.9 | 84.1 | 96.9 | 90.0 |
| Chlorite | Uncalcined | 73.0 | 48.6 | 65.3 | 36.4 |
| | 1200° C. | 100.2 | 52.4 | 90.4 | 77.6 |
| Saponite | 1000° C. | 99.7 | 80.6 | 98.8 | 92.6 |
| Feldspar | — | 99.3 | 21.3 | 88.8 | 59.1 |
| Magnesium Carbonate | — | 49.2 | 12.1 | 8.5 | 0.2 |
| Magnesium Hydroxide | — | 7.6 | 25.2 | 1.7 | 0.2 |
| Magnesium Oxide | — | 0.5 | 9.0 | 1.0 | 3.9 |
| Magnesium Phosphate | — | 69.3 | 17.6 | 31.5 | 0.6 |
| Pumice, Coarse | — | 98.8 | 86.7 | 96.6 | 71.8 |
| Pumice, Fine | — | 97.8 | 85.9 | 96.1 | 70.9 |
| Pumice, Flour | — | 89.3 | 68.5 | 81.3 | 56.7 |

The foregoing data are supportive of the significant improvement in dental health that may be achieved by utilizing dental prophylactic compositions containing the calcined mineral particle agents of this invention.

We claim:

1. A dental prophylaxis preparation comprising, as its principle cleaning and polishing constituent, particles of a calcined mineral selected from the group consisting of smectite, sepiolite, and chlorite minerals, substantially none of the calcined particles being retained on an 80 mesh screen, essentially all of the calcined particles passing through a 100 mesh screen, with the median particle size lying in the range of about 10-40 microns, the calcined particles being predominantly of the magnesium metasilicate form and having a lamellar crystal structure comprising superimposed layers of two-dimensional silica tetrahedra and two-dimensional octahedra.

2. A preparation, as claimed in claim 1, wherein the particles are calcined at a temperature in the range from about 800° C. to about 1200° C.

3. A preparation, as claimed in claim 1, and further containing a water-soluble, non-toxic anticariogenic adjuvant selected from the group consisting of water-soluble fluoride-containing salts and water-soluble aluminum ion-containing salts.

4. A preparation, as claimed in claim 1, wherein the calcined mineral particles are present at a level of about 30-95% by weight of the preparation.

5. A method of cleaning and polishing the teeth comprising the application thereto of a dental prophylaxis preparation comprising, as its principal cleaning and polishing constituent, particles of a calcined mineral selected from the group consisting of smectite, sepiolite, and chlorite minerals, substantially none of the calcined particles being retained on an 80 mesh screen, essentially of the calcined particles passing through a 100 mesh screen, with the median particle size lying in the range of about 10-40 microns, the calcined particles being predominantly of the magnesium metasilicate form and having a lamellar crystal structure comprising layers of superimposed two-dimensional silica tetrahedra and two-dimensional octahedra.

6. A method as claimed in claim 5, wherein the particles are calcined at a temperature in the range from about 800° C. to about 1200° C.

7. A method, as claimed in claim 5, and further containing a water-soluble, non-toxic anticariogenic adjuvant selected from the group consisting of water-soluble fluoride-containing salts and water-soluble aluminum ion-containing salts.

8. A method, as claimed in claim 5, wherein the calcined mineral particles are present at a level of about 30-95% by weight of the preparation.

* * * * *

UNITED STATES PATENT AND TRADEMARK OFFICE
CERTIFICATE OF CORRECTION

PATENT NO. : 4,418,053

DATED : November 29, 1983

INVENTOR(S) : Joseph C. Muhler and Mark S. Putt

It is certified that error appears in the above—identified patent and that said Letters Patent is hereby corrected as shown below:

Col. 2, line 29, "ae" should be --are--.

Col. 2, line 60, "an" should be --and--.

Col. 3, line 43, "particles." should be --particles,--.

Col. 4, line 41, "anti-cariogenic" should be --anticariogenic--.

Col. 6, line 27, "$Al_4Si_8O_{20})(OH)_4$." should read --$Al_4Si_8O_{20}(OH)_4$.--.

Col. 7, lines 16-17, "micrograph" should be --micrographs--.

Col. 7, line 39, "defind" should be --defined--.

Col. 7, line 68, "curing" should be --during--.

Col. 9, line 5, "belived" should be --believed--.

Col. 10, line 12, "on" (second occurrence) should be --in--.

UNITED STATES PATENT AND TRADEMARK OFFICE
CERTIFICATE OF CORRECTION

PATENT NO. : 4,418,053

DATED : November 29, 1983

INVENTOR(S) : Joseph C. Muhler and Mark S. Putt

It is certified that error appears in the above—identified patent and that said Letters Patent is hereby corrected as shown below:

Col. 10, line 34, "in" should be --to--.

Col. 12, line 20, "os" should be --of--.

Col. 13, line 18, "substituted" should be --substantiated--.

Col. 13, line 37, "of" should be --the--.

Col. 14, line 7, "darknes" should be --darkness--.

Col. 17, line 30, "principle" should be --principal--.

Col. 18, line 31, "of the" should be --all of the--.

Signed and Sealed this

Sixteenth Day of October 1984

[SEAL]

Attest:

GERALD J. MOSSINGHOFF

Attesting Officer

Commissioner of Patents and Trademarks